(12) United States Patent
Zhou et al.

(10) Patent No.: US 6,490,032 B1
(45) Date of Patent: Dec. 3, 2002

(54) METHOD AND APPARATUS FOR IMPROVING A DARK FIELD INSPECTION ENVIRONMENT

(75) Inventors: Hao Zhou, Aliso Viejo, CA (US); William D. Jimenez, Mission Vieji, CA (US); Travis L. Smith, Corona, CA (US)

(73) Assignee: Newport Fab, LLC, Newport Beach, CA (US)

( * ) Notice: Subject to any disclaimer, the term of this patent is extended or adjusted under 35 U.S.C. 154(b) by 161 days.

(21) Appl. No.: 09/583,593

(22) Filed: May 31, 2000

(51) Int. Cl.⁷ .............................................. G01N 21/00
(52) U.S. Cl. ................... 356/237.4; 356/237.5; 356/237.6; 250/372; 118/723 R; 156/345
(58) Field of Search ............... 356/237.1–237.6, 356/336–343; 250/372, 358.1, 359.1, 360.1, 572; 118/723 R, 504; 158/345, 643.1, 656.1, 659.11

(56) References Cited

U.S. PATENT DOCUMENTS

| | | | | |
|---|---|---|---|---|
| 3,580,685 A | * | 5/1971 | Eriksson | 356/237.1 |
| 4,570,207 A | * | 2/1986 | Takahashi et al. | 362/152 |
| 5,493,123 A | * | 2/1996 | Knollenberg et al. | 356/237.1 |
| 5,545,289 A | * | 8/1996 | Chen et al. | 156/643.1 |
| 5,909,276 A | * | 6/1999 | Kinney et al. | 356/237.1 |
| 5,968,275 A | * | 10/1999 | Lee et al. | 118/723 R |
| 6,157,449 A | * | 12/2000 | Hajduk | 356/364 |

OTHER PUBLICATIONS

Applicant is not aware of any patents, publications, or other information for consideration by the Patent Office.

* cited by examiner

Primary Examiner—Frank G. Font
Assistant Examiner—Sang H. Nguyen
(74) Attorney, Agent, or Firm—Farjami & Farjami LLP

(57) ABSTRACT

An apparatus and method is disclosed for facilitating a dark field inspection. The workpiece inspection apparatus comprises three sides and a light-blocking top and defines a dark field inspection area. Light incident on the top is substantially blocked while a clean room environment is maintained by allowing air to permeate through the top.

29 Claims, 4 Drawing Sheets

METHOD AND APPARATUS FOR IMPROVING A DARK FIELD INSPECTION ENVIRONMENT

FIELD OF THE INVENTION

The present invention relates generally to an apparatus and method for detecting workpiece defects and, more particularly, to a dark field inspection apparatus and method for detecting defects on a workpiece in a clean room environment.

BACKGROUND OF THE INVENTION

Workpieces such as, for example, wafers, are typically in the form of a flat, substantially planar disk. Workpieces may include semiconductor wafers, magnetic disks and optical disks. For many applications, particularly in the area of integrated circuits, the wafer serves as a high-tech building block. In order to produce quality microelectronic devices, it is desirable that the wafer surface be uniform, planar and devoid of any imperfections.

Chemical mechanical planarization (CMP) is an abrasive process used for polishing the surface of the wafer. The CMP process involves the use of chemical slurries and a circular (sanding) action to polish the surface of the wafer. Slurry is a chemical polishing agent deposed upon the wafer while on a polishing pad. After the polishing step, the wafer is cleaned and rinsed to remove the slurry. A wafer may undergo several steps of cleaning, rinsing, polishing and drying in the CMP machine to remove any debris from the wafer surface. For example, the manufacture of a semiconductor wafer generally includes "layering" dielectrics or metals on the wafer surface. After each layer is formed, the wafer surface is typically cleaned, polished, rinsed and dried. The smooth surface is now ready for further processing steps or for the next layer to be applied to the surface.

The CMP process to some degree smooths out minor defects in the wafer surface which result from, for example, slicing the wafer from a silicon ingot. However, the CMP process itself can introduce or reveal several types of yield-limiting defects, including residual slurry, surface voids and surface particles. Residual slurry remaining on the wafer as a result of inadequate cleaning can unevenly raise the surface level.

Wafer surface defects are considered "events" that lead to or can lead to electrical faults in microelectronic circuitry. The events are first identified and then reviewed to determine if they represent defects that can adversely affect subsequent device performance. Defects are found on both patterned and unpatterned wafers. An unpatterned wafer is a bare silicon wafer or a wafer with various blanket films coated thereon. A patterned wafer has undergone a photolithography process wherein geometric shapes have been transferred to the surface of the wafer.

A surface void is a divot on the wafer surface caused by an embedded particle (e.g., dust) or a weak point in the top layer that is ripped out or dislodged during processing. For example, a small foreign particle may be "coated" on the surface during the layering step and subsequently dislodged from the surface. Thus, a void or dimple remains where the particle once was. Alternatively, surface particles may adhere to the surface after the layering step resulting in a small rise (mound) in the surface. Similarly, the dielectric or metal used in the layering step may become contaminated with a trapped particle prior to or during the layering step. Once applied, the layer will exhibit "rough" areas where contaminates are present.

Microscratches on the wafer surface are caused by small particles, debris or similar foreign objects caught between the polishing pad and the wafer surface. During the polishing step, the particle causes a "scratch" on the wafer surface. In some cases, the microscratch may be inadvertently filled with a deposited material (e.g., tungsten) during a tungsten CMP process application.

After the wafer has undergone a CMP process, including layering the wafer with dielectrics or metals, the wafer proceeds to a photolithography process. Photolithography is a means for transferring shapes from a mask to the surface of a wafer, producing a patterned wafer. The steps involved in the photolithographic process will be briefly discussed. First, the wafer is chemically cleaned to remove any remaining foreign matter from the surface such as, for example, traces of organic, ionic and metallic impurities.

Silicon dioxide ($SiO_2$) maybe deposited on the surface to serve as a barrier layer, whereupon a photoresist maybe applied to the surface. The wafer is spun at a high speed, called "spin coating," to produce a thin uniform layer of photoresist on the surface. Traditionally, there have been two types of photoresist, positive and negative. Negative resists were common in the earlier years of integrated circuit processing, but more recently positive resists are the prevalent type of resist used in VLSI (very-large-scale-integration) fabrication processes. For positive resists, the wafer is exposed with UV (ultraviolet) light wherever the underlying material is to be removed. In this resist, exposure to the UV light changes the chemical structure of the resist so that it becomes more soluble in the developer. The exposed resist is then washed away by the developer solution, leaving windows of the bare underlying material. The mask used contains an exact copy of the pattern which is to remain on the wafer.

The photoresist coating becomes photosensitive, or imagable, after a soft-baking step. During soft-baking, nearly all of the solvents are removed from the photoresist coating. If considerable solvent remains in the coating, the positive resist may be incompletely exposed.

The mask is a glass plate with a patterned emulsion of metal film on one side. The mask must be aligned with the wafer in the location that the pattern is to be transferred to the surface. The glass plate is a lens which directs the UV light onto the wafer. Exposure time can vary depending upon, for example, the sensitivity of the resist and the lens aperture. Once aligned, the photoresist is exposed through the pattern on the mask with a high intensity UV light, creating on the wafer surface a "printed" replica of the mask pattern.

The wafer is then placed in a developer solution until the resist becomes completely soluble (i.e., for positive resists), and then hard-baked to improve adhesion of the photoresist to the wafer surface and to cure the photoresist.

While not as common as in the CMP process, defects can and do occur during the photolithographic process. Briefly, the defects caused by photolithography can be grouped into three areas; (1) defects in the resist material, (2) problems with the pattern or equipment, and (3) errors in the printing or exposing processes. The photoresist material may become contaminated with a foreign particle, material or substance prior to spin-coating. As a result, the photoresist will contain small spurious particles causing an event. Additionally, residual resist (resist remaining after the developer step) creates "webbing" between the printed lines on the wafer during the exposure step.

A printing defect can result from anomalies on the pattern. Any damage to the pattern (e.g., scratches) can affect the wafer duplication. Lastly, printing errors can cause defects such as, for example, a "bridging" between two printed lines and large areas of unexposed photoresist.

Wafer manufactures ambitiously attempt to prevent defects due to the substantial threat of reduction in final wafer yields. Typically wafer production takes place in a clean room environment. A clean room is broadly defined as an uncontaminated or nearly uncontaminated room which is maintained for the manufacture or assembly of objects, e.g., semiconductor wafers. U.S. Federal standard 209E catagorizes clean rooms into classes defined by the levels of air cleanliness expressed in number of particles per cubic measure. For example, a class 100 room must have less than 100 particles per cubic foot; a class 10 room must have less than 10 particles per cubic foot, and so on. In general, as the class room number decreases, the number of particles per cubic measure allowed decreases.

Many of the particles present in the air, on clothing and on skin, if brought in to contact with a workpiece, can fatally contaminate the workpiece (i.e., workpiece must be discarded). Contaminates may include dust particles, skin, hair, body oils, fibers, and even small living organisms such as dust mites. Potentially, each of these contaminates can fall on a workpiece or in a material used to "coat" the workpiece and subsequently result in an event.

Workpiece (e.g., wafer) defects can be reduced by limiting contaminates in the manufacturing room to less than 10 particles per cubic foot (class 10). To achieve such a low rate of "loose" particles in the air, on the equipment and on the human operators, clean room technologies are employed. Continuous air flow, ventilation and filtration are essential to maintaining low particle count. Hepa filters may be installed in the ceiling and floor to continuously draw air in for particle filtering. The floors may be raised in a grid-like fashion to allow air venting under foot. The operators can comfortably walk atop the grids without noticing the spacing between the grids which allows air and large contaminates to flow through the raised floor. This reduces the risk of operators "picking up" fallen particles while working in the clean room.

Perhaps the most common source of contaminates and the hardest to control in a clean room environment are human contaminates. Skin fragments and hair follicles are continually shed from the human body. Each time a workpiece is handled by a human operator, skin, hair and body oils may be inadvertently transferred from the human to the workpiece surface. To prevent this, operators are typically required to wear full body suits made from lint-free material. Nearly every inch of human skin is covered as well as the operator's shoes. The head is hooded with several layers of material to keep hair from dropping in the room. The nose and mouth must also be covered to help prevent particles from being cast into the air during exhale. Again, clean room ventilation plays an important part in filtering the air to collect exhaled particles.

Even with the precautions mentioned above, wafer defects nonetheless occur during manufacture (e.g., CMP and photolithography). Wafer defect detection, analysis, and resolution play an important role in keeping wafer processes and yields under control. In fact, as long as there has been semiconductor manufacturing, and more particularly VLSI circuitry, defect inspection has been vital to identifying sources of potential electrical faults. As disclosed previously, the types of defects can vary depending upon which production stage the defect originates (e.g., pre-CMP, post-CMP, lithography). Many manufacturers must perform intermittent inspections throughout production searching for different types of defects each time.

Companies such as KLA-Tencor Corp. have introduced high tech tools for patterned and unpatterned wafer inspection. For example, KLA-Tencor's AIT II is a patterned defect inspection tool that offers automated double-dark field (DDF) laser scanning technology, real-time signal processing algorithms, and an automatic defect classification for analysis. The Surfscan®SP1 inspection tool, designed by KLA-Tencor, performs highly sensitive inspection of unpatterned wafers. The SP1 features multiple dark field collection optics and an optional bright field channel and can detect and classify defects on all types of unpatterned surfaces. An advanced feature of the SP1 called Surface NanoTopography® (SNT) provides quantitative measurements of topography variations with nanometer sensitivity over millimeter ranges.

New process technologies such as CMP introduce unknown classes of surface defects requiring companies to continuously update and advance their latest defection tools. As wafer manufacturing processes increase in complexity, defect detection costs are driven up. For example, an automated wafer detection tool as previously described can cost the wafer manufacturer $500,000 or more, and with each new advanced feature further increasing the overall cost. Keeping up with defect detection may pose a daunting economic challenge even the largest semiconductor manufacturers.

Human inspectors may also be employed to inspect workpieces and can after spot defects as small as 0.5 $\mu$m. Typically, not every wafer is inspected, but rather a statistical sampling of wafers is inspected from a particular cassette or lot. In practice, the operator removes a wafer from a cassette and inspects the wafer for surface defects. Because the CMP and photolithography processes are generally performed on a cassette or "lot" of wafers at a time, a periodic sampling of the cassette should give an accurate account of any post-production defects present in the entire cassette. If the inspector discovers a defect on a sampled wafer, additional wafers may be inspected from the cassette. Upon discovery of a defect, the inspector may view the wafer under a microscope located at the inspector's inspection station. Microscope viewing is also useful for "spot-checking" the printed lines on the wafer and may be performed at any time during the inspection process.

As previously discussed, a photoresist pattern is duplicated onto the wafer surface. FIG. 1 illustrates an exemplary resist pattern atop an oxide layer which is coated on the wafer surface. Both the resist patterns 100 and the oxide layer 125 are light transparent, therefore light can pass through to the wafer surface 150 where it is reflected back. Light which is directed on-axis to the wafer 130 is high intensity and can be easily detected with the human eye. The reflected light 140 is substantially equal in intensity to the incoming light 130 and is equally easily detected by the human eye.

Light photons are scattered from the edge of the resist features 160. The scattered light intensity is much less than the intensity of the incoming 130 or reflected light 140 and, hence, the contrast is very low making it extremely difficult to detect the patterned resist. Defects in the pattern are even more difficult to spot over the high intensity incoming and reflected light. To avoid this problem, the high intensity light is blocked to create a "dark field option." The scattered light from the edge of the resist features is more easily seen in a dark field option.

Presently known dark field methods used by inspectors are grossly inadequate and include simulating a dark field by physically holding a covering over the wafer. Simply, the inspector uses one hand to hold an opaque, such as black or similar non-transparent hue, piece of paper over the workpiece (e.g., wafer) and the other hand to hold the workpiece. Ideally, the paper will block the surrounding light thus creating a dark field to view the wafer. In practice, however, to effectively block the light from all angles, the paper has to completely encompass the wafer or at least encompass the sides, top and back. Holding a light shielding structure large enough to adequately surround the dimensions of the wafer (i.e., wafers average about 8 to 10 inches in diameter), while permitting the inspector to move the wafer to observe the surface, is cumbersome and awkward.

Current dark field techniques are not well suited to a proper clean room environment. Even with the extensive measures discussed above for a class 10 clean room, particles such as dust, clothing fibers and debris are still present near the inspector's work station. Introduction and movement of objects at or near the station causes the particles to "stir" and become afloat in the air. Proper ventilation at the inspection station helps to draw loose particles from the air into the filter systems either above or below the station. Presently, each time the inspector readjusts the handheld dark field structure, particles are stirred-up and set afloat. The air between the structure and the wafer is filled with loose particles which can drop upon the wafer. The structure does not contain adequate ventilation to draw the particles away from the wafer because even the smallest hole in the structure would allow light to shine through and thus destroy the operator's dark field.

Accordingly, there exists a need for a workpiece inspection method and apparatus that is cost effective yet reliable. More particularly, there is a need for a dark field inspection method and apparatus to assist human inspectors in detecting workpiece, such as for example, wafer, defects. Further, there is a need for a method and apparatus that enables wafer inspectors to undergo defect detection with a dark field option while maintaining the integrity of a clean room environment.

SUMMARY OF THE INVENTION

The present invention overcomes the problems outlined above and provides an improved method and apparatus for workpiece inspection. More particularly, the present invention provides a dark field option for workpiece inspection particularly useful in a clean room application. A preferred embodiment of the present invention comprises a structure having three sides and a multi-dimensional top. Air is allowed through the top surface of the structure.

In a preferred embodiment, a dark field inspection structure includes a top having a plurality of spaced-apart slats. The slats of each layer are offset from the slats of the next layer. The offset configuration substantially blocks the incident light by either reflecting or absorbing the light. A spacing defined by each slat and layer of slats permits air to flow through the top.

In one embodiment, the inspection structure comprises a substantially opaque and antistatic material.

In another embodiment, the inspection structure comprises a thin slot for transporting a workpiece.

BRIEF DESCRIPTION OF THE DRAWINGS

These and other features, aspects, and advantages of the present invention will become better understood with reference to the following description, appended claims, and accompanying drawings where:

DETAILED DESCRIPTION OF PREFERRED EMBODIMENTS

The present invention relates to an improved dark field inspection apparatus and method for detecting the presence of defects on a workpiece in a clean room environment. The apparatus and method may be suitable for inspection of a variety of workpieces, such as magnetic and optical disks, however, the present invention is conveniently described in the context of semiconductor wafers. Although described and illustrated in the context of semiconductor wafers, it is not intended that the invention be limited to the illustrated embodiment.

A dark field inspection method is preferred by human inspectors of wafer defects. In a dark field (low light intensity), light scattered from the resist features of a wafer is more readily detected. By substantially blocking the incoming light and providing a high contrast light area, a dark field option is created thus allowing the inspector to view low contrast defects.

Figure 1:
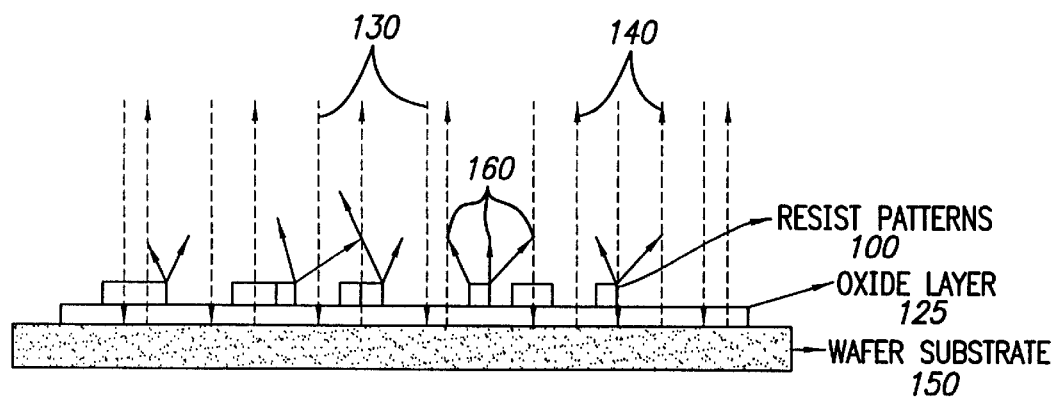
FIG. 1 illustrates light incident upon a wafer substrate having an exemplary resist pattern.
Figure 2:
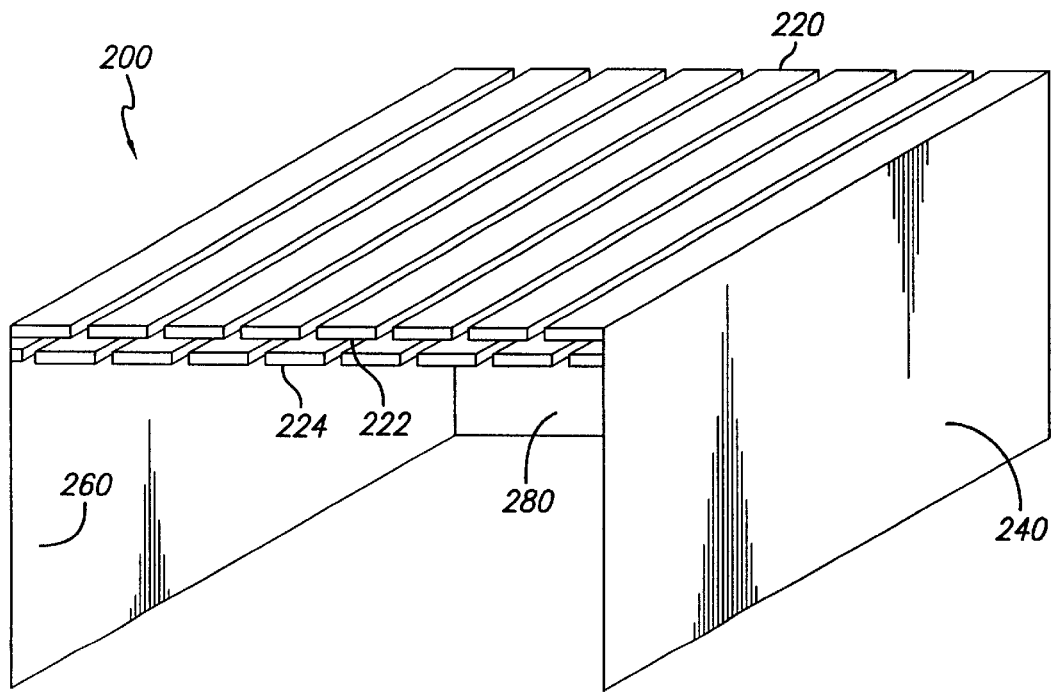
FIG. 2 illustrates an apparatus having a multi-layered slat top surface in accordance with one embodiment of the present invention.

Referring now to FIG. 2, dark field inspection apparatus 200 comprises a light blocking top surface 220. In an exemplary embodiment, top surface 220 comprises a first layer 222 and a second layer 224. For illustrative purposes, two layers are depicted and described, however it should be appreciated that inspection apparatus comprising more or less than two layers are within the scope of the present invention.

Respective layers 222 and 224 each suitably comprise a plurality of substantially planar slats. The number and dimension of slats are merely illustrative and not intended to limit the scope of the present invention. It will become apparent to one skilled in the art that any number of slats orientated in an array of directions (e.g., layers 222 and 224 may be rotated 90°) is within the scope of the present invention.

Apparatus 200 further comprises sides 240, 260, 280 attached to top surface 220. In one embodiment, apparatus 200 is placed atop a flat surface such as a clean room work table (not shown) with the lower edges of sides 240, 260, 280 in contact with the table surface. In another embodiment the contact points of sides 240, 260, 280 are secured to the table surface.

In yet another embodiment, apparatus 200 comprises a substantially opaque material, (e.g., an opaque acrylic) to absorb the radiant light incident on sides 240, 260 and back 280. Top 220 also suitably comprises an opaque or partially opaque material to block the incident light. In a preferred embodiment, apparatus 200 comprises a black or similar dark-colored material.

Viewing light is defined herein as the light allowed in through the open side. This side is open to facilitate workpiece inspection by the inspector. Non-direct light rays are able to enter the apparatus through the open side. By avoiding direct light contact with the workpiece, high contrast is maintained and "glare" is substantially eliminated. Viewing light further includes light at angles incident to a bottom layer (e.g., layer 224) of top 220 which reflects upward to a next layer (e.g., layer 222) then reflects back to the bottom layer and so on until eventually the light passes through the bottom layer. However, in a preferred embodiment, substantially all the incident light on top 220 is absorbed by an opaque material and therefore virtually no light will be reflected.

Figure 3:
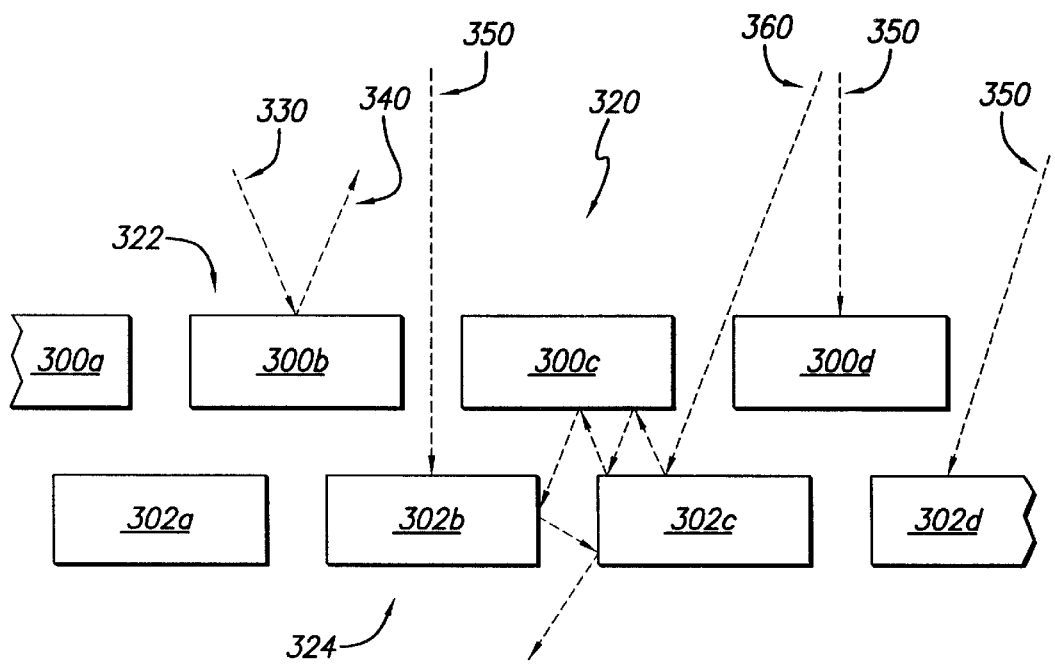
FIG. 3 illustrates an enlarged side view of the top of the apparatus shown in FIG. 2 in accordance with one embodiment of the present invention.

Referring now to FIG. 3, the interaction between incident light and an exemplary slat configuration is shown. A light source (not shown) having light rays 330, 350 and 360 is suitably positioned to deliver light rays on top 320 of an apparatus in accordance with the present invention. Exemplary top 320 comprises a top layer 322 and a bottom layer 324 of spaced-apart slats. For illustrative purposes only, top layer 322 comprises slats 300a–300d and bottom layer 324 comprises slats 302a–302d.

In one embodiment, the plurality of slats comprises a reflective material. Light ray 330, illustrated incident to slat 300b at an angle, is reflected from the slat and returned in an angled direction as light ray 340. Light ray 360 is also shown at an angle which is reflected upward from slat 302c to slat 300c and back to slat 302c and so on, until eventually light ray 360 has passed through top 320 and enters in the inspection area.

In an alternative embodiment, the apparatus including top 320 comprises an absorbing opaque material. With continued reference to FIG. 3, light rays 350 are shown incident to top 320 and are substantially absorbed by slats 300d, 302b and 302d.

The horizontal spacing between the slats can vary depending upon the application. For example, the present inventors have found that a three-to-one (3 to 1) ratio of slats to space substantially blocks the incoming light yet airflow is maintained. Preferably, the horizontal spacing is small in comparison to the width of each slat. As the number of layers of slats becomes greater than two, the horizontal spacing between the slats may increase or decrease depending on the horizontal widths of the slats.

With continued reference to FIG. 3, exemplary layer 322 is offset from layer 324 by, for example, one half period. The period of offset can be changed as long as the incident light remains substantially blocked. Those skilled in the art will recognize that there are many variations of layer patterns, spacing and offsets which fall within the scope of the present invention.

Wafer inspection is typically carried out in a clean room environment (i.e., low particle count in the air). Referring again to FIG. 2, apparatus 200 of the present invention is suitably configured and designed to be compatible with the clean room environment. Preferably, apparatus 200 is constructed from a material having anti-static characteristics (either occurring naturally in the material or being treated) including but not limited to, acrylic, plastic, glass, an any other anti-static and clean room grade material known in the industry. The sides 240, 260 and 280 of apparatus 200 are preferably secured to top 220 with an epoxy or similar adhesive having substantially dust-free and particle-free qualities.

Continuous air flow and filtration of and around the clean room inspection station is key to maintaining a low particle count. Typically, air filters are installed in the ceiling and/or the floors to continuously draw air for filtering. Referring again to FIG. 3, layers 322 and 324 are separated by a small vertical spacing. Air can easily flow through the horizontal and vertical spacing of top 320, thus allowing particles to be drawn through the inspection station to the filters. It is important to filter the air inside apparatus 200 to prevent loose particles from falling upon the wafer to be inspected.

Figure 4:
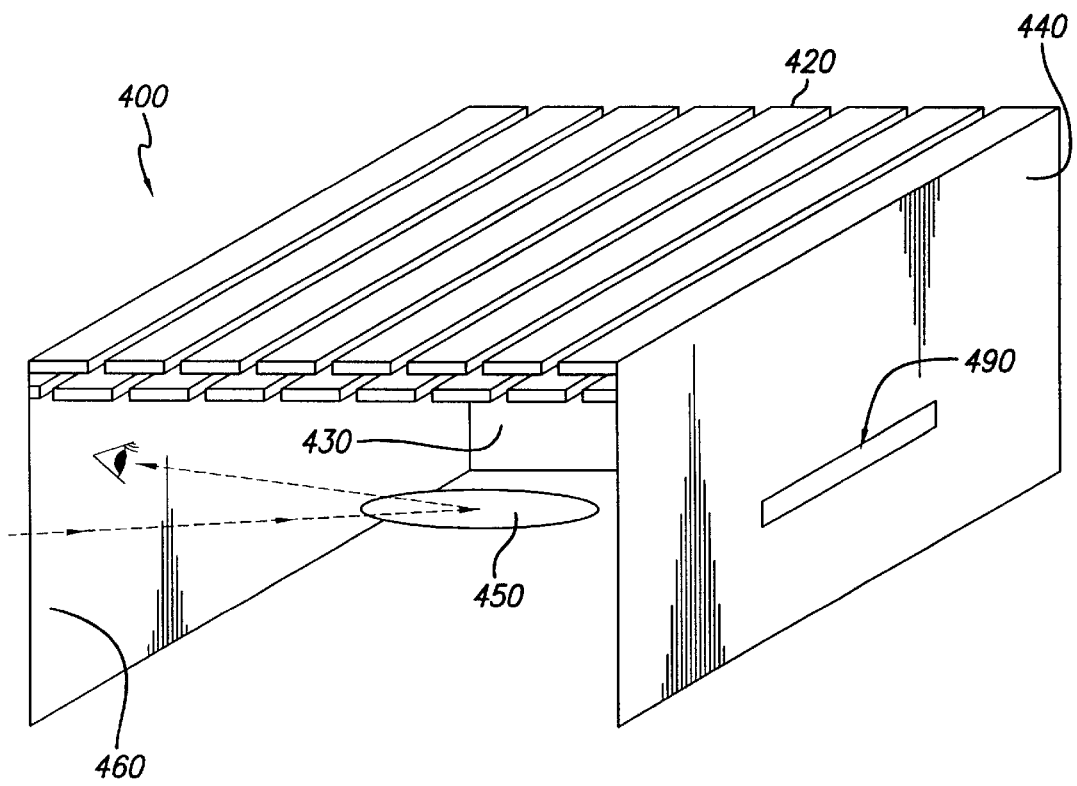
FIG. 4 illustrates in plain view another embodiment of the dark field inspection apparatus of the present invention.

With reference to FIG. 4, apparatus 400 in accordance with one embodiment of the present invention comprises a top 420 and sides 430, 440 and 460. A workpiece 450 is transported from inside apparatus 400 through a small opening 490 in side 440. Although pictured in side 440, a similar slot can be included in sides 430 and 460. It is preferable that opening or slot 490 be just wide enough to allow the workpiece to pass without obstruction from apparatus 400. It is desirable to keep the workpiece from touching the apparatus surface during transport and viewing to avoid contamination. Workpiece 450 may be transported through slot 490 using a robotic arm (not pictured) located in or near the inspection station area.

The desired dark field is realized by substantially blocking the incident light on top 420 using a configuration in accordance with the invention herein disclosed and limiting the incident light at the viewing (open) side of the apparatus. Thus, the inspector may readily spot low contrast defects on a workpiece such as a wafer. Once inside apparatus 400, no particular placement of the wafer is required, only that the wafer be placed for adequate viewing by the inspector, which can vary between inspectors.

Air can circulate around the wafer and the inspection area through the spacing of top 420. Particles present in and around the inspection area are drawn through the spacing or through the open side near the inspector. Preferably apparatus 400 is affixed to a clean room table and remains stationary at all times, thus reducing the amount of "stirring-up" of particles around the wafer and inspection station.

Indirect light enters the inspection area through the open side of apparatus 400 as shown by the broken line on FIG. 4. The light scatters from defects present on the workpiece and reflects away from the workpiece. The high contrast field created by substantially eliminating the overhead high intensity light, reduces the glare and allows the inspection to see the low contrast defects.

Figure 5A:
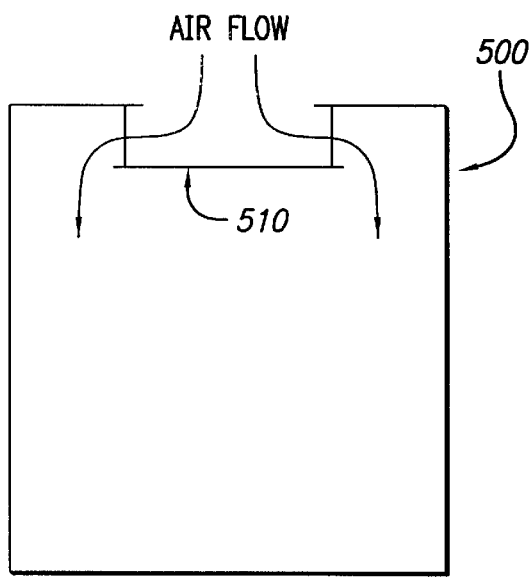
FIG. 5A illustrates a frontal view of a recessed top surface in accordance with another embodiment of the present invention.
Figure 5B:
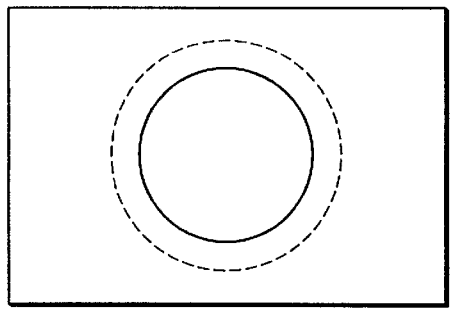
FIG. 5B illustrates a top view of the embodiment of FIG. 5A.

Referring now to FIGS. 5–7, alternative embodiments of the dark field apparatus in accordance with the present invention are illustrated. Apparatus 500 of FIGS. 5A and 5B comprises a light restricting top having a recessed portion 510. FIG. 5B is an exemplary top view of apparatus 500. Air can flow through an opening in the top and reach the inside inspection area. Recessed portion 510 can be suitably maneuvered to allow more or less air passage.

Figure 6A:
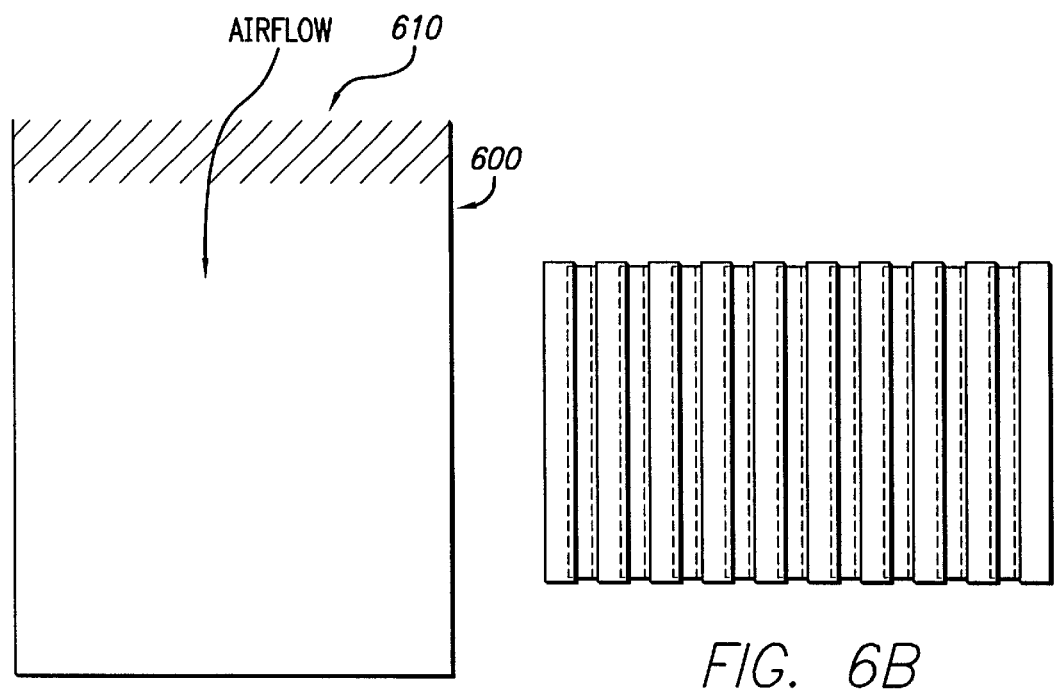
FIG. 6A illustrates a frontal view of an angled top surface in accordance with yet another embodiment of the present invention.
Figure 6B:
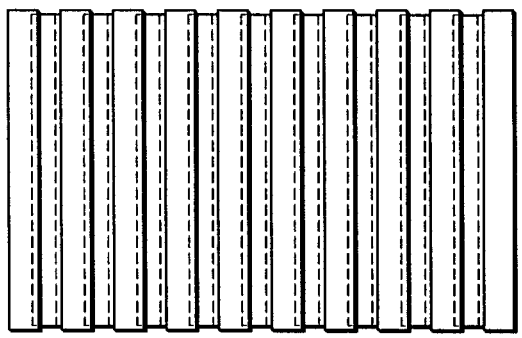
FIG. 6B illustrates a top view of the embodiment of FIG. 6A.

FIGS. 6A and 6B illustrate an apparatus 600 comprising a top having a single layer of slats 610. FIG. 6B is an exemplary top view of apparatus 600. Slats 610 are suitably angled to block incident light rays yet allow air to flow through to the inspection area inside. In a preferred embodiment, apparatus 600 comprises a plurality of adjustable slats 610. In a blind-like manner, the incline angle of slats 610 can be changed according to room lighting and filtering limitations.

Figure 7A:
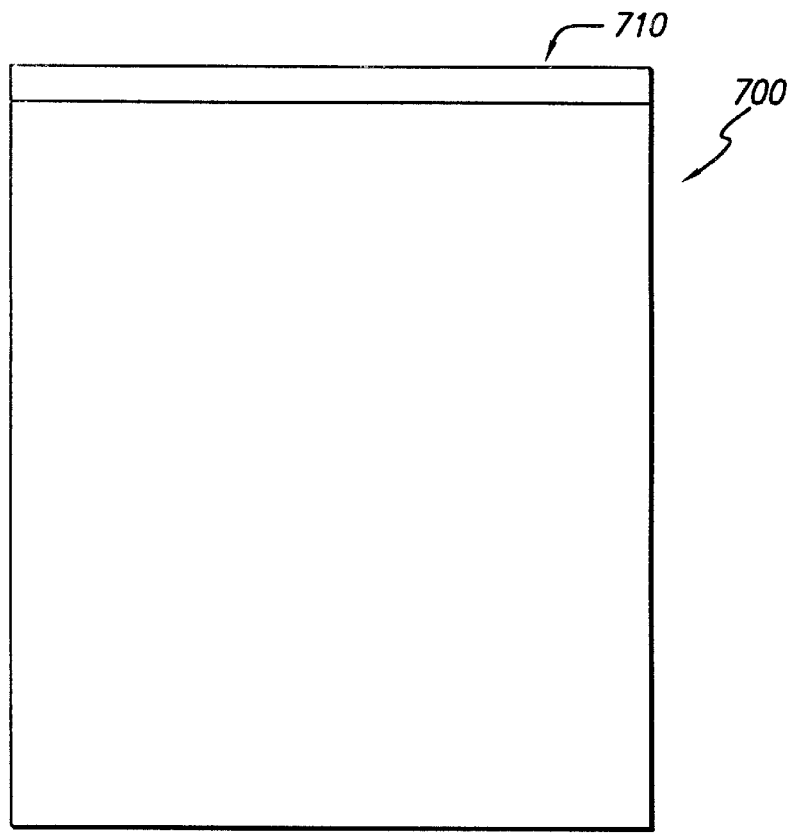
FIG. 7A illustrates a frontal view of an angled top surface in accordance with another embodiment of the present invention.
Figure 7B:
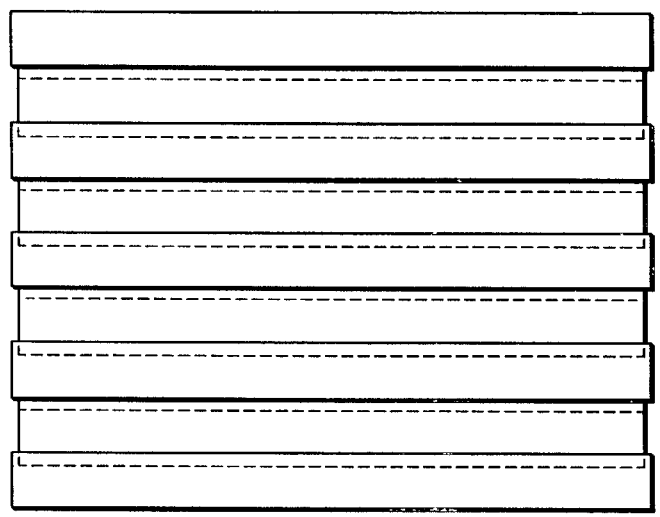
FIG. 7B illustrates a top view of the embodiment of FIG. 7A.

FIGS. 7A and 7B illustrate yet another embodiment in accordance with the present invention. Apparatus 700 comprises a single layer of angled slats 710. FIG. 7B is a top view of apparatus 700. Similar to slats 610, slats 710 are preferably angled, however slats 710 are rotated a quarter turn to accommodate for particular lighting, filtering and viewing needs. Preferably, slats 710 are movable in a blind-like manner to increase or decrease the angle of inclination of each slat.

It should be appreciated that the particular implementations shown and described herein are illustrative of the invention and its best mode and are not intended to otherwise limit the scope of the present invention in any way.

The present invention has been described above with reference to preferred embodiments. However, those skilled in the art having read this disclosure will recognize that changes and modifications may be made to the preferred embodiments without departing from the scope of the present invention. For example, the number of layers forming the top of the dark field apparatus; the number, size and placement of the slats of each layer of the top; and the spacing between the slats and layers of the top may be modified without departing from the spirit of the present invention. These and other changes are intended to be included within the scope of the present invention, as expressed in the following claims.

What is claimed is:

1. A workpiece inspection apparatus for use in a clean room inspection area comprising:
   a first side portion;
   a second side portion;
   a back portion attached to said first and second side portions; and
   a top portion attached to said first and second side portions and said back portion, said top portion having at least two layers comprising a first layer and a second layer, said first layer and said second layer being separated by an air space, said first layer comprising a first plurality of substantially horizontal slats and said second layer comprising a second plurality of substantially horizontal slats, said first and said second plurality of substantially horizontal slats being suitably positioned to substantially block incident light on said top portion.

2. The apparatus of claim 1 comprising a substantially opaque material.

3. The apparatus of claim 1 comprising a black material.

4. The apparatus of claim 1 wherein said first side portion includes a workpiece transportation slot.

5. The apparatus of claim 1 wherein said first plurality of substantially horizontal slats is misaligned with said second plurality of substantially horizontal slats.

6. The apparatus of claim 5 wherein said first plurality of substantially horizontal slats is misaligned by one half period from said second plurality of substantially horizontal slats.

7. The apparatus of claim 1 wherein said air space allows air to flow through said top portion and around a workpiece placed inside said apparatus.

8. The apparatus of claim 1 comprising an opaque acrylic having anti-static characteristics.

9. A method for darkfield inspection of a workpiece in a clean room environment comprising the steps of:
   enclosing an inspection area with a substantially opaque apparatus having at least three sides and a top, said top comprising a plurality of slats;
   positioning said slats in a formation to substantially block light incident on said top;
   permitting airflow through said formation;
   placing said workpiece within said inspection area; and
   viewing said workpiece in said inspection area.

10. The method of claim 9 further comprising the steps of:
   removing said workpiece from a container of workpieces; and
   replacing said workpiece in said container.

11. The method of claim 10 wherein said replacing step comprises a robotic arm.

12. The method of claim 9 wherein said positioning step comprises forming two layers of slats.

13. The method of claim 12 wherein said positioning step comprises vertically misaligning the slats of the two layers.

14. The method of claim 13 wherein said positioning step comprises misaligning by one half period.

15. The method of claim 9 wherein said positioning step comprises a single layer of angled slats.

16. The method of claim 15 wherein said positioning step comprises changing the angle of inclination of said slats.

17. A darkfield wafer inspection structure for use at an inspection station wherein said inspection station comprises an inspection table and said structure is mounted on said table, said structure comprising a top portion attached to three side portions, said side portions blocking light incident on said side portions and said top portion blocking light incident on said top portion, said top portion having an opening, said opening permitting air to flow into an inspection viewing area.

18. The structure of claim 17 comprising a substantially opaque and anti-static material.

19. The structure of claim 17 comprising a black material.

20. The structure of claim 17 wherein said top portion comprises a grid configuration having a plurality of substantially planar slats separated by small air spaces.

21. The structure of claim 20 wherein said grid configuration comprises a single layer of slats.

22. The structure of claim 20 wherein said grid configuration comprises a single layer of movable slats.

23. The structure of claim 17 wherein said top portion comprises two layers wherein each layer is a horizontal grid and said layers are in vertical misalignment.

24. The structure of claim 17 wherein said top portion comprises a recessed portion.

25. A dark field inspection station for use in the visual examination of workpieces, said inspection station comprising:
   a shroud defining a dark field inspection space; and
   a top of said shroud comprising a plurality of slats, said plurality of slats blocking light rays incident on said top, said plurality of slats permitting the flow of air through said top and through said inspection space.

26. The inspection station of claim 25 wherein said plurality of slats form a single layer of angled slats.

27. The inspection station of claim 26 wherein said layer of angled slats is adjustable in response to the degree of desired airflow.

28. The inspection station of claim 25 wherein said top comprises two levels.

29. The inspection station of claim 28 wherein one of said levels protrudes within said inspection space.

* * * * *